United States Patent [19]

Vo-Dinh

[11] Patent Number: 5,306,403
[45] Date of Patent: Apr. 26, 1994

[54] RAMAN-BASED SYSTEM FOR DNA SEQUENCING-MAPPING AND OTHER SEPARATIONS

[75] Inventor: Tuan Vo-Dinh, Knoxville, Tenn.

[73] Assignee: Martin Marietta Energy Systems, Inc., Oak Ridge, Tenn.

[21] Appl. No.: 933,376

[22] Filed: Aug. 24, 1992

[51] Int. Cl.$^5$ ............... G01N 27/447; G01N 27/26
[52] U.S. Cl. ........................ 204/182.8; 204/299 R
[58] Field of Search ............ 204/299 R, 182.8, 180.1; 73/61.58, 51.54

[56] References Cited

U.S. PATENT DOCUMENTS 4,674,878 6/1987 Vo-Dinh ........................... 386/301

OTHER PUBLICATIONS

T. W. Graham Solomms, Organic Chemistry, John Wiley & Sons 1980.

Theodora W. Greene, Protective Groups In Organic Synthesis, John Wiley & Sons 1981.

Giulietta Smulevich et al. "Surface-Enhanced Resonance Raman Spectra of Adriamycia, 11-Deoxycarminomycin, Their Model Chromophores, and Their Complexes with DNA" Journal of Physical Chemistry, vol. 90, No. 23 (1986) 6388-6392.

Therese M. Cotten et al. "Determination of Purine Bases by Reversed-Phase High Performance Liquid Chromatography Using Real-Time Surface-Enhanced Raman Spectroscopy" Analytical Chemistry, vol. 63, No. 5 (1991) 437-442.

Jean-Marie L. Séquaris et al. "Direct Analysis of High-Performance Thin-Layer Chromatography Spots of Nucleic Purine Derivatives by Surface-Enhanced Raman Scattering Spectrometry" Analytical Chemistry, vol. 59, No. 3 (1987) 525-527.

R. Ken Force et al. "Surface-Enhanced Raman Spectroscopy at a Silver Electrode as a Detection System in Flowing Streams" Analytical Chemistry, vol. 62, No. 7 (1990) 678-680.

Therese M. Cotton et al. "Flow Injection Analysis and Real-Time Detection of RNA Bases by Surface-Enhanced Raman Spectroscopy" Analytical Chemistry, vol. 62, No. 18 (1990) 1958-1963.

Primary Examiner—John Niebling
Assistant Examiner—John S. Starsiak, Jr.
Attorney, Agent, or Firm—Edward A. Pennington; Joseph A. Marasco; Harold W. Adams

[57] ABSTRACT

DNA sequencing and mapping are performed by using a Raman spectrometer with a surface enhanced Raman scattering (SERS) substrate to enhance the Raman signal. A SERS label is attached to a DNA fragment and then analyzed with the Raman spectrometer to identify the DNA fragment according to characteristics of the Raman spectrum generated.

15 Claims, 6 Drawing Sheets

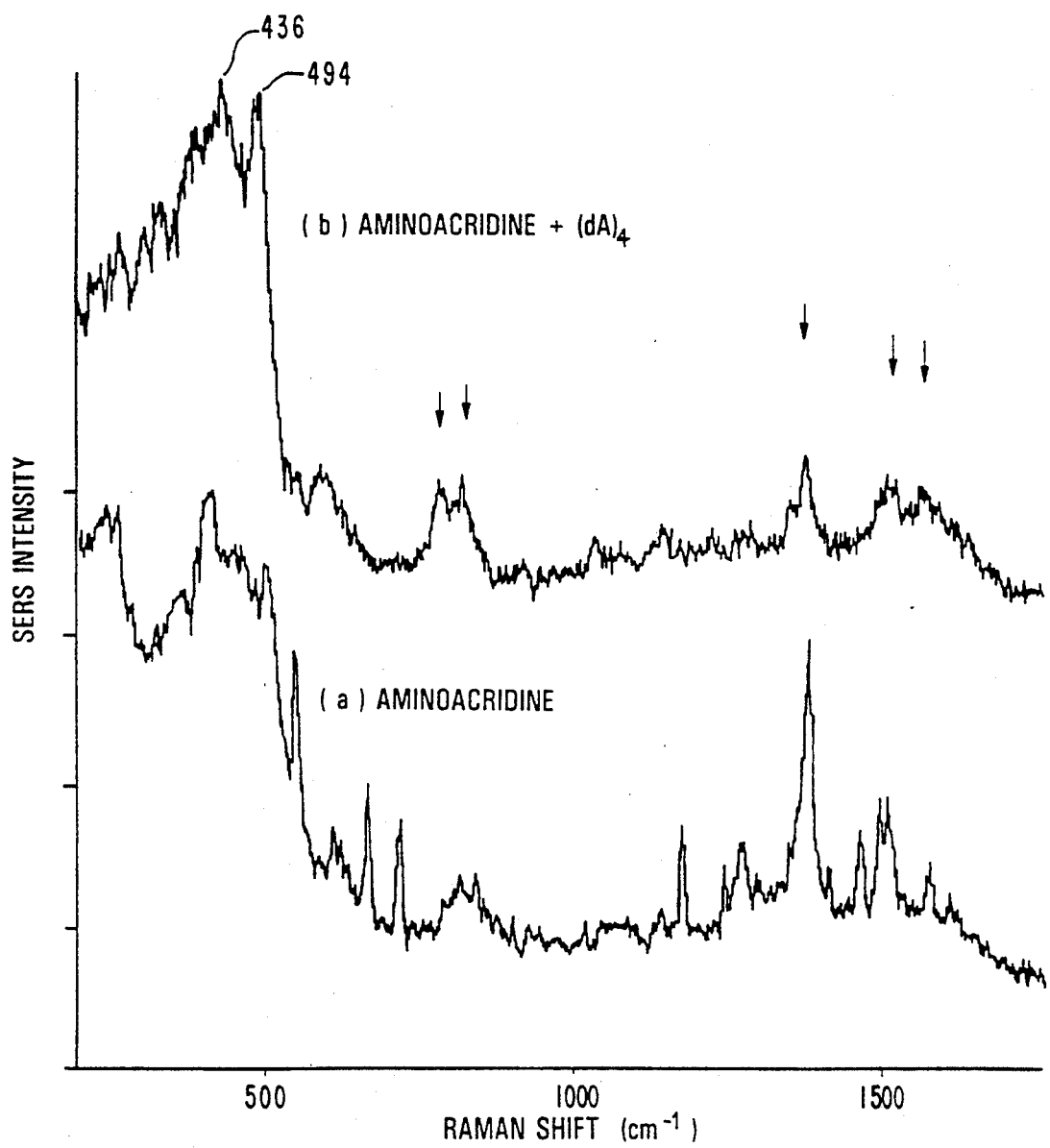

RAMAN-BASED SYSTEM FOR DNA SEQUENCING-MAPPING AND OTHER SEPARATIONS

This invention was made with Government support under contract DE-AC05-84OR21400 awarded by the U.S. Department of Energy to Martin Marietta Energy Systems, Inc. and the Government has certain rights in this invention.

FIELD OF THE INVENTION

The present invention relates generally to biochemical separation and identification techniques based on Raman spectroscopy and, more specifically, to the use of Raman-based spectroscopy incorporated into a DNA sequencing technique.

BACKGROUND OF THE INVENTION

Spectroscopy is an analytical technique concerned with the measurement of the interaction of radiant energy with matter and with the interpretation of the interaction both at the fundamental level and for practical analysis. Interpretation of the spectra produced by various spectroscopic instrumentation has been used to provide fundamental information on atomic and molecular energy levels, the distribution of species within those levels, the nature of processes involving change from one level to another, molecular geometries, chemical bonding, and interaction of molecules in solution. Comparisons of spectra have provided a basis for the determination of qualitative chemical composition and chemical structure, and for quantitative chemical analysis.

One particular spectroscopic technique, known as Raman spectroscopy, utilizes the Raman effect, which is a phenomenon observed in the scattering of light as it passes through a material medium, whereby the light suffers a change in frequency and a random alteration in phase. Raman spectroscopy is a spectrochemical technique that is complementary to fluorescence, and has been an important analytical tool due to its excellent specificity for chemical group identification. One of the major limitations of Raman spectroscopy is its low sensitivity. Recently, the Raman technique has been rejuvenated following the discovery of enormous Raman enhancement of up to 106 for molecules adsorbed on microstructures of metal surfaces.

Deoxyribonucleic acid (DNA) is the main carrier of genetic information in most living organisms. DNA is essentially a complex molecule built up of deoxyribonucleotide repeating units. Each unit comprises a sugar, phosphate, and a purine or pyrimidine base. The deoxyribonucleotide units are linked together by the phosphate groups, joining the 3' position of one sugar to the 5' position of the next. The alternate sugar and phosphate residues form the backbone of the molecule, and the purine and pyrimidine bases are attached to the backbone via the 1' position of the deoxyribose. This sugar-phosphate backbone is the same in all DNA molecules. What gives each DNA its individuality is the sequence of the purine and pyrimidine bases.

The resolution of the genetic material of an organism into linear sequence of the material's elements is known as "genetic mapping". In decreasing order of size these elements include the chromosome, the genes. the codons, and the nucleotides of the DNA. Complete mapping of the genetic material of an organism implies the complete description of its DNA sequences. This has been achieved in only a few cases, with small viruses with sequences only a few thousand nucleotides long. Higher plants or animals have vastly longer sequences.

Current DNA sequencing techniques are based on two methods developed in the late 1970's. Most previous research efforts have been devoted to automation of existing sequencing methods and the use of fluorescent labels. Two of the most prominent sequencing techniques are known respectively as the Sanger method and the Maxam-Gilbert method. In both, radiolabeled DNA fragments are generated chemically or enzymatically. The DNA fragments are then separated on a molecular weight basis using polyacrylamide gel electrophoresis. The gels are dried and autoradiographed to image the DNA band pattern. The band pattern is interpreted to yield sequence information, and the sequence data are entered into a computer for further analysis.

Although these sequencing methods are very useful, they suffer from several notable limitations. For example, the radioactive labels used for detection present a potential health hazard. These radioisotopes are also unstable and expensive for large-scale applications. Moreover, they require highly trained personnel and their disposal often creates serious environmental and safety problems.

L. M. Smith et al, in *Nature*, Vol. 321, p. 674 (Jun. 12, 1986), describes a fluorescence method for partial automation of DNA sequence analysis. The detection of the DNA fragments obtained by the Sanger method is performed by measuring the emission of a fluorescent label covalently attached to the oligonucleotide primer used in enzymatic DNA sequence analysis. Four different types of fluorescent labels were used for each of the reactions specific for the bases adenosine (A), cytosine (C), guanosine (G), and thymidine (T). The reaction mixtures are combined and co-electrophoresed down a single polyacrylamide gel tube. The basic structure of the Smith et al. sequencer is illustrated in FIG. 1. The sequencer includes upper and lower buffer reservoirs 10 and 12 between which extends a polyacrylamide gel column 14. The fluorescent bands of DNA are detected near the bottom of the tube 14 with a detector 16 and the sequence information is acquired directly by a computer 18. An idealized output of the sequencer is illustrated in FIG. 2.

Another system for DNA sequencing in which four chemically related, yet distinguishable fluorescence-tagged dideoxynucleotides are used to label DNA by a modified Sanger protocol has been recently developed by Prober et al., as described in *Science*, 238, 336 (1987). It was suggested that the fluorescent sequencing fragments are resolved temporally rather than spatially in a single band by conventional polyacrylamide electrophoresis. The dyes used are a family of 9-(carboxymethyl)-3-hydroxy-6-oxo-6H-xanthines or succinylfluoresceins. These fluorophores have largely overlapping yet distinct emission bands. The automated sequencer is capable of determining 50 bases per hour per lane. A fully loaded gel thus yields a throughput of about 600 bases per hour.

There has been little progress made in the development of advanced detection technologies that will provide new or improved systems for DNA sequence detection and analysis. Current instruments use straightforward fluorescence detection with optical filters. These detection techniques are based solely on a single spectroscopic method which may be prone to misreading errors. For example, the fluorescence spectra of the three chemical dyes or "labels" NBD (4-chloro-7-nitrobenzo-2-oxa-1-diazole), Texas Red dye, and Fluorescein, which are commonly used for DNA sequencing, are broad, structureless and overlap one another severely.

Thus, there is a need for new or improved methodologies and instrumentation that will improve the accuracy, speed and efficiency of DNA sequencing.

SUMMARY OF THE INVENTION

An object of the present invention is to provide a Raman-based DNA sequencing method and apparatus that is capable of accurate, fast and efficient DNA sequencing.

Another object of the present invention is to provide a Raman-based DNA sequencing method and apparatus that is capable of providing an understanding of the human genome structure in general and the mutagenic and carcinogenic effects of energy-related environmental pollutants in particular.

Another object of the present invention is to provide a Raman-based DNA sequencing method and apparatus that provides improved DNA sequence detection and is useful for analyzing new DNA labels, nucleotides or oligonucleotides that cannot be monitored by other spectroscopic methods.

These and other objects of the invention are met by providing an apparatus which combines Raman spectroscopy with DNA sequence analysis. The sensitivity of the Raman spectroscopic component is enhanced by surface enhancement, thus providing a surface-enhanced Raman spectroscopy (SERS) system for DNA sequencing.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

FIG. 6 is another SERS spectrum generated in accordance with the present invention, and showing a comparison of aminoacridine;

DETAILED DESCRIPTION OF THE PREFERRED EMBODIMENTS

DNA sequencing or mapping require the identification of a DNA fragment (or series of oligonucleotides). The present invention requires the attachment of a surface enhanced Raman scattering (SERS) label on the DNA fragments/probes for sequencing or mapping applications. The label is a specific chemical group that can be detected using the SERS spectrographic technique. Raman spectroscopy is a spectrochemical technique that is complementary to fluorescence, and is an important analytical tool due to its excellent specificity for chemical group identification. In the past, Raman Spectroscopy was considered limited because of its low sensitivity. Recently, however, enormous Raman enhancement of up to $10^8$ for molecules adsorbed on microstructures of metal surfaces. See, for example, D. J. Jeanmaire and R. P. Van Duyne *J. Electronal. Chem.*, 84, (1977).

Figure 1:
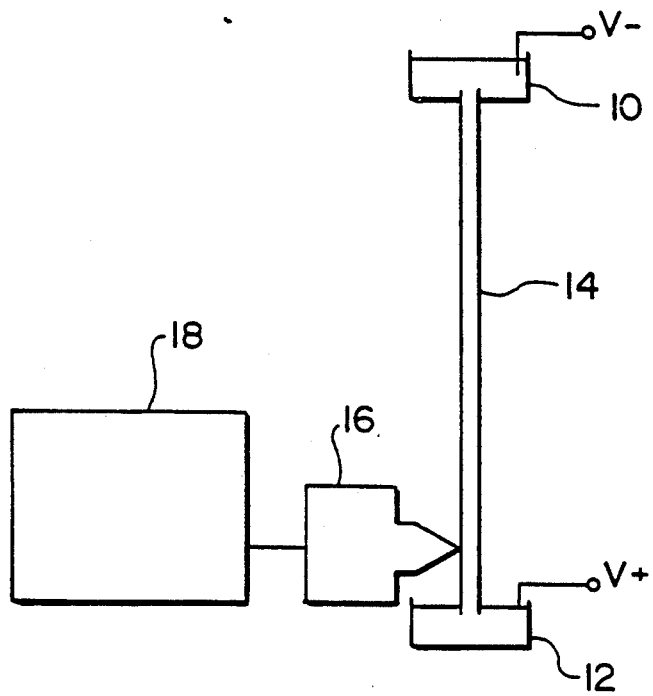
FIG. 1 is a schematic view of a sequencer according to the prior art.
Figure 2:
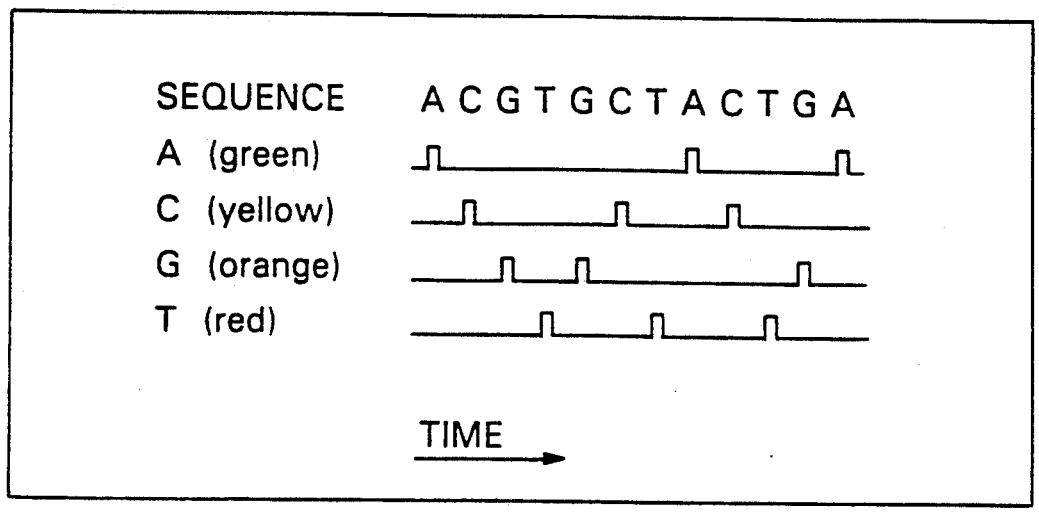
FIG. 2 is a schematic view of an idealized output from the automated DNA sequencer of FIG. 1.
Figure 3:
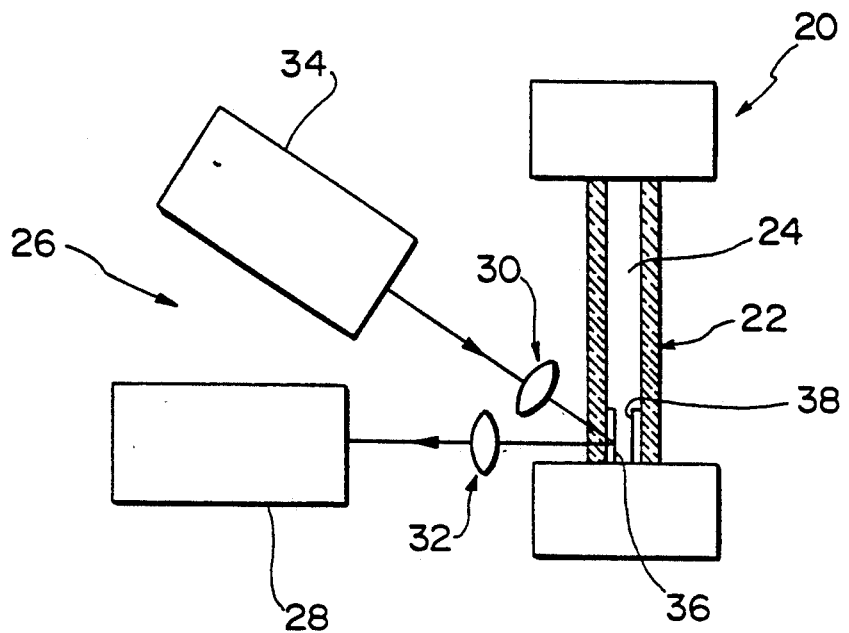
FIG. 3 is a schematic view of an apparatus for analyzing DNA according to one embodiment of the present invention.

A basic SERS apparatus for analyzing a DNA fragment (or series of ligonucleotides) is illustrated in FIG. 3. A sequencer 20 is used to physically separate the DNA fragments labelled with a SERS label. Various types of separation techniques could be employed, including gel electrophoresis, capillary electrophoresis, thin-layer chromatography, paper chromatography, mass spectrometry, etc. In the embodiment of FIG. 3, an enclosure 22 is formed by two parallel quartz glass plates. The plates enclose a gel 24 in which the DNA fragments are disposed. The sequencer 20 depicts known technology for separating the DNA fragments.

A SERS detection system 26 includes a detector 28, focusing optics 30, 32 and a light source 34. After separation of the DNA fragments, the SERS labels are detected when they are still bound onto the DNA fragments by focusing the light source, preferably a laser, onto the surface of a SERS-active coating 36 and 38. A SERS spectroscopic apparatus suitable for use in the present invention is described in U.S. Pat. No. 4,674,878 to Vo-Dinh, which is incorporated herein by reference. The detector 28 of the aforementioned patent includes a monochromator and photon counter which sends signals to a multi-channel analyzer and a rate meter, so that the light signals can be interpreted.

As shown in FIG. 3, a laser beam is focused onto the surface of the SERS-active coating 36 inside the enclosure 22. Scattered radiation is then collected by the detector 28 at an angle of 30°–60° with respect to the exciting beam. A SERS spectrum generated by the detector 28 is then analyzed for DNA sequencing and/or mapping or other operations.

Instrumentation for the above-described embodiment is commercially available. The SERS measurements can be conducted with a Spex Model 1403 double-grating spectrometer equipped with a gallium-arsenide photomultiplier tube (RCA, Model C31034) operated in the single-photon counting mode. Data storage and processing is performed by a Spex Datamate computer. The laser source is a 514.5 nm line argon-ion laser from SpectraPhysics, Model 166 and a 647.1 nm line of a krypton-ion laser (Innova 70, Coherent). The laser power is preferably set at 50 mW. The SERS coating can be a 75 nm thick layer of silver on alumina.

To prepare the coatings, glass microscope slides are cut into rectangular strips and cleaned. Alumina suspended in water is placed on the glass slide to cover the whole surface of the glass with alumina. The coated glass slide is then spun at 2000 rpm for 20 seconds on a spinning device to uniformly spread the alumina on the glass surface. The slides are then placed in a vacuum evaporator to receive a deposit of silver. Silver deposition is done at a pressure of $2 \times 10-6$ Torr with a deposition rate of 2 nm/s. When placed inside the enclosure, the slides with the SERS-active coatings are used to provide a SERS spectra when scanned with the Spex instrument. The spectra data is recorded in the computer and then analyzed.

In the FIG. 3 embodiment, the coatings 36 and 38 may be located at the bottom of the enclosure 22 as illustrated, so as to adsorb separated DNA fragments after separation. Either or both of the glass plates or sides of the enclosure may be coated directly, without using glass slide inserts. The coatings may extend the full length of the enclosure so that the length of the enclosure can be scanned during separation using one or more SERS spectrometer devices to make real time measurements. The process described above for coating the microscope slides could be used to coat the inside surfaces of the glass plates of the enclosure.

Figure 4:
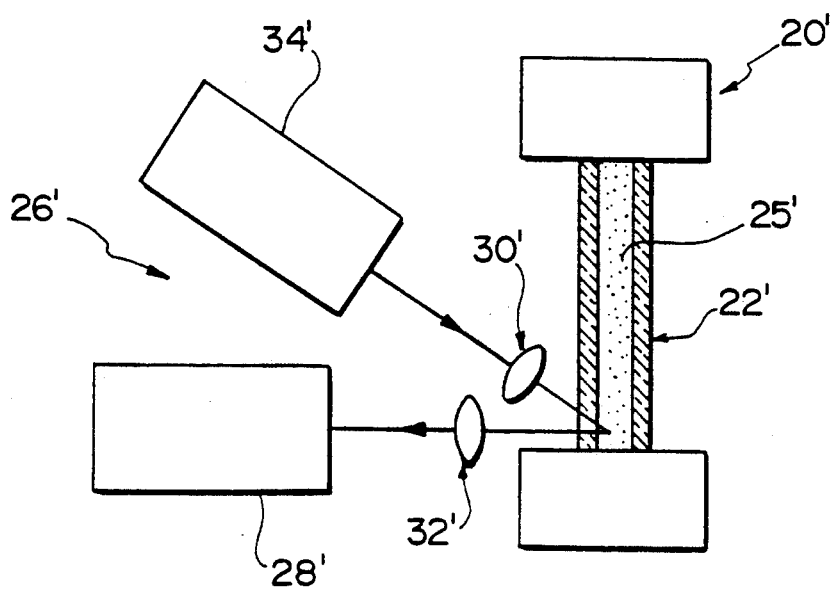
FIG. 4 is a schematic view of an apparatus for analyzing DNA according to another embodiment of the present invention.

A variation of the FIG. 3 embodiment is illustrated in FIG. 4, in which similar components have the same but primed reference numerals. Instead of having a coating on the inner surfaces of the gel plates, the gel itself contains a SERS-active species 25' dispersed therein. The SERS-active species may be metal sols, or microparticles, such as those described in U.S. Pat. No. 4,674,878, which is incorporated herein by reference.

EXAMPLE 1

Figure 5:
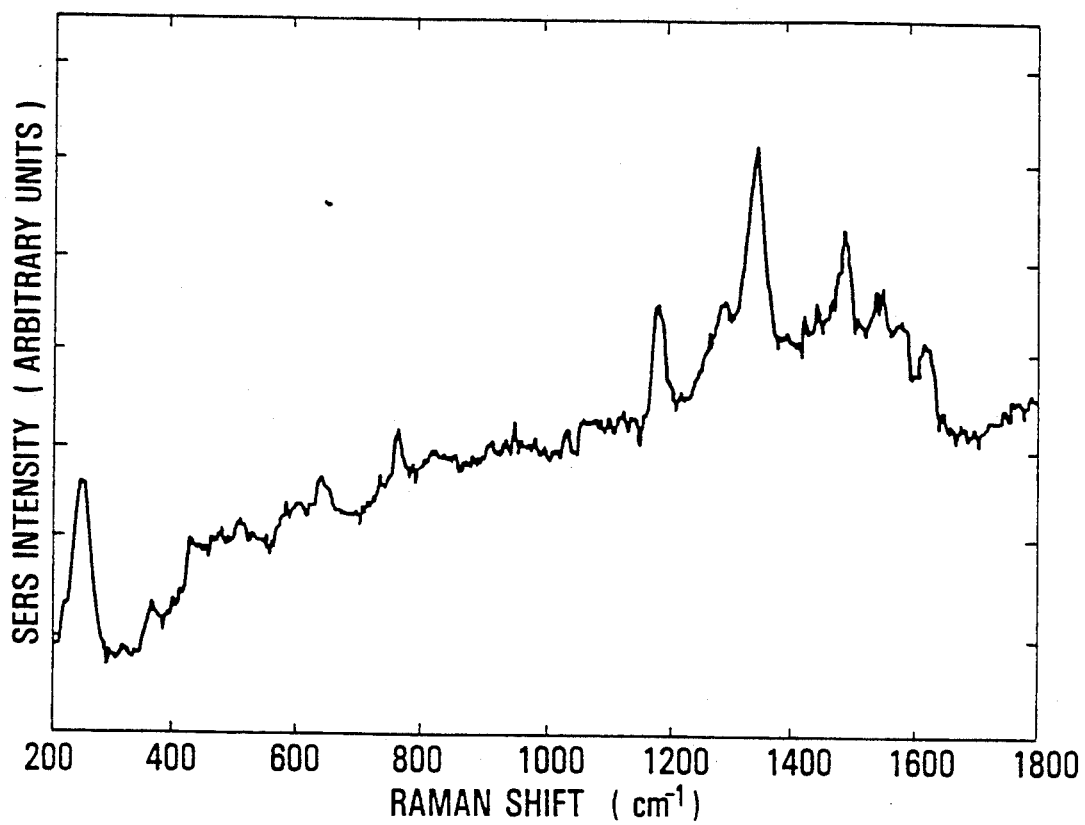
FIG. 5 is a SERS spectrum generated in accordance with the present invention.

FIG. 5 is a SERS measurement of a label known as TRIT, which is a dye often used for DNA sequencing. The spectrum was obtained in situ from a 0.05 mg/ml solution (50% ethanol/$H_2O$) of TRIT using a glass plate covered with silver-coated $TiO_2$ as the substrate. The glass plate would correspond to one of the surface coatings 36 and 38 of FIG. 3.

The SERS substrate was placed directly inside a quartz glass enclosure, such as enclosure 22 of FIG. 3, in which the dye solution was contained. A laser beam was focused into the SERS substrate inside the enclosure and the scattered radiation was collected at an angle of 90° with respect to the exciting beam. FIG. 5 shows that TRIT has several SERS bands. The strongest band occurs at 1370 cm−1. Several moderately strong bands (770 cm−1, 1198 cm−1, and 1514 cm−1) are also present in the SERS spectrum of the dye. The SERS spectrum of TRIT also shows weak bands at 644 cm−1, 1314 cm−1, 1078 cm−1, 1606 cm−1, and 1642 cm−1. Overall, the SERS bands of TRIT are very narrow, and the bands are well resolved from one another.

For the embodiment of FIG. 3, the SERS label material are preferably from a chemical group not found in DNA (e.g., sulfur compounds, thio groups, chemical groups containing Sn, Al, Cd, Eu, Te, etc.) Since these chemical groups are not found in DNA fragments, they exhibit Raman and SERS bands that are not interfered with by the DNA fragments.

EXAMPLE 2

FIG. 6 represents further evidence of the feasibility of the in situ detection technique corresponding to the embodiments of either FIG. 3 or FIG. 4. In particular, the attachment of aminoacridine, used as a model SERS label, was performed using the following procedure. The terminal 5'-phosphate of an oligonucleotide was reacted with a water soluble carbolimide in imidazole buffer to yield the 5'-phosphorimidazolide. Exposure of the phosphorimidazolide to amino-acridine in aqueous solution resulted in the production of stable phosphoramidate containing the aminoacridine label. The production of stable phosphoramidate was described in C. C. F. Chu et al., *Nucleic Acids Research*, 11, 6513, (1983).

Trace "(a)" of FIG. 6 shows the SERS signal of aminoacridine, while trace "(b)" shows the SERS signal of a four-oligonucleotide fragment (containing a base sequence of four adenines) having an aminoacridine label bound to it. Several typical SERS peaks of the free aminoacridine are distinctly observed in the SERS spectrum of the labelled oligonucleotide fragment, as seen in trace (b) at arrows 1385, 1512, and 1574 cm−1.

This example used aminoacridine as the SERS label since extensive information on the SERS characteristics of aminoacridine is available. One can also use other SERS labels that contain a chemical group not found in DNA and which exhibit Raman and SERS bands that are not interfered by the DNA fragments.

EXAMPLE 3

Figure 7A:
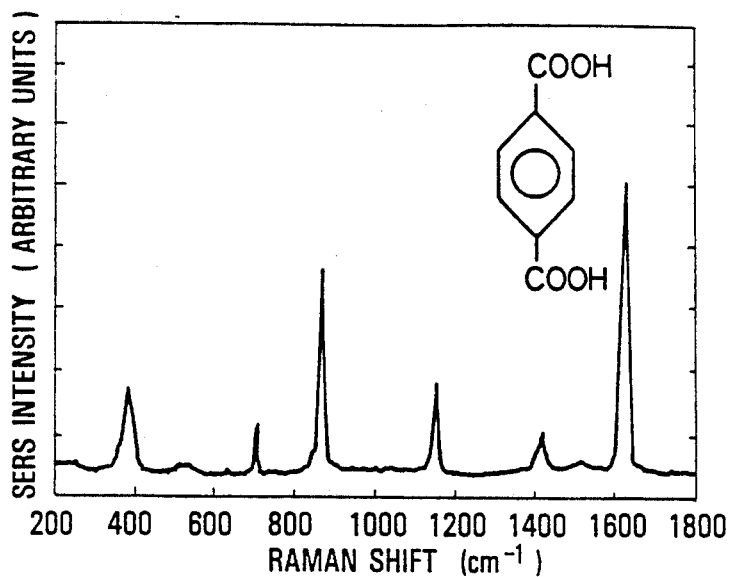
FIGS. 7(a)-(c) are SERS spectra generated in accordance with the present invention.
Figure 7B:
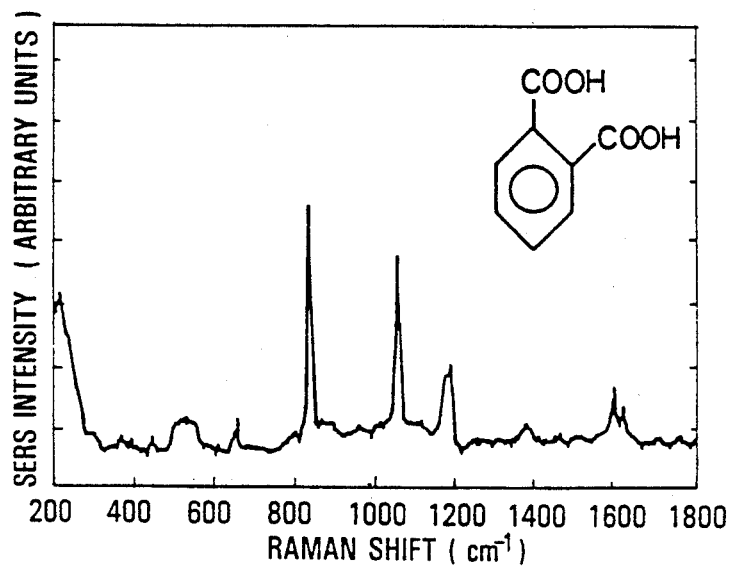
Figure 7C:
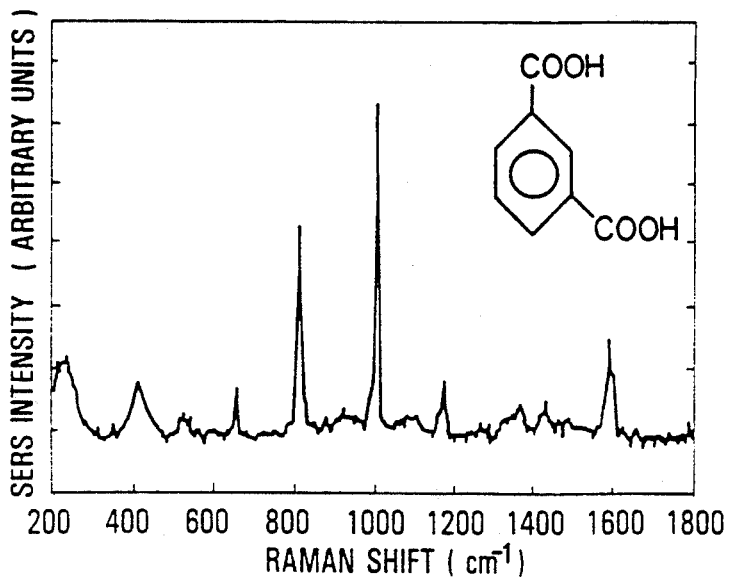
Figure 8:
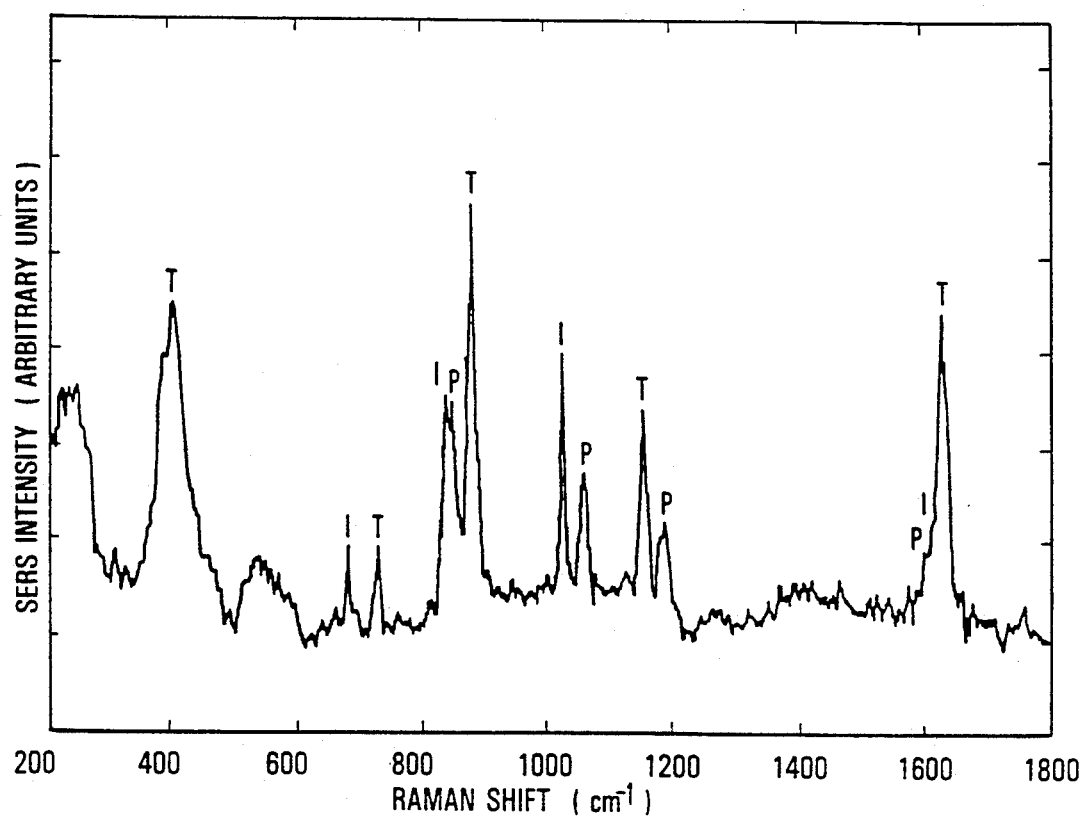
FIG. 8 is another SERS spectrum generated in accordance with the present invention.

Referring to FIGS. 7(a)–(c) and 8, a SERS analysis is used to distinguish three isomers of dicarboxylic acid of benzene. FIGS. 7(a)–(c) show the SERS spectra of (a) 0.5 ppm terephthalic acid, (b) 2 ppm phthalic acid, and (c) 1 ppm isophthalic acid, respectively. It should be noted that these isomers have exactly the same molecular weight. If they were to be used as Raman labels on DNA sequencing primers, the three different isomers would be expected to demonstrate minimal or negligible differences among themselves in terms of affecting mobility of the resulting DNA fragments. However, as shown in FIG. 8, the SERS spectra of each is readily distinguishable in a mixture of all three isomers. FIG. 8 is a SERS spectrum of a ternary mixture of the three isomers. The different isomers are abbreviated as "T" for terephthalic acid, "P" for phthalic acid, and "I" for isophthalic acid. FIG. 8 thus illustrates the excellent resolving power of the SERS technique when using these and similar labels to effect DNA sequencing. Another important feature of the SERS spectra of these compounds not shown in the FIGS. 7(a)–(c) and 8 is the subattomole detection sensitivity due to the SERS effect, thus enhancing the effectiveness of the Raman based system.

Figure 9:
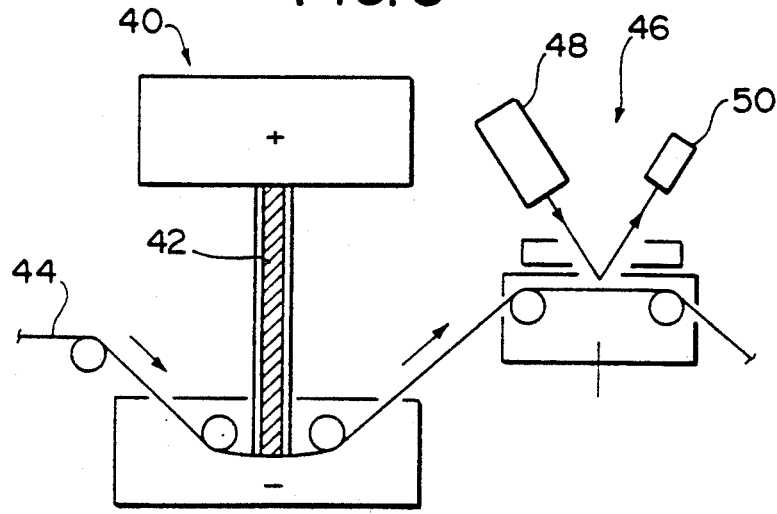
FIG. 9 is an apparatus for analyzing DNA in accordance with another embodiment of the present invention.

In the embodiments of FIGS. 3 and 4, the SERS labels were attached to the DNA fragments or oligonucleotides and, after separation of DNA fragments, the SERS labels can be detected when they are still bound to the DNA fragments. A variation of this technique would involve detecting the SERS labels after the SERS labels are selectively detached from the DNA fragments and transferred onto a SERS substrate. The latter case is analogous to blotting procedures used in sequencing and mapping. FIG. 9 is a schematic view of a SERS apparatus for analyzing DNA which provides indirect analysis whereby the SERS labels are selectively detached from the DNA fragments onto the SERS substrates. The sequencer 40 includes an enclosure 42 which provides a running gel. A conveyor belt-type blotting membrane 44 runs across the bottom of the enclosure. As separated fragments electrophorese off the bottom of the gel, they are bound to the membrane 44 that moves them to the detection system 46. The detection system includes a light source 48 which outputs a laser beam which is focused onto the surface of the membrane 44. The membrane 44 has a SERS-active material on the surface thereof. A light detector 50 collects scattered light and processes same into a readable output, such as a trace showing wavelength and SERS intensity. The structure described with reference to FIG. 9 can be used for direct blotting and for automated multiplex sequencing with a moving SERS substrate.

Various methods can be used to detach the SERS labels from the DNA fragments. In one example, the SERS labels can be attached using a chemical bond that is specifically broken by varying certain parameters such as pH, temperature, etc. In another example, various chemical reactions can be used to break specific linker bonds in order to detach labels from DNA fragments. In another example, a laser beam is tuned to a specific frequency to break a particular linker bond. The temperature of the laser radiation can be used to help detach the bond. Further examples include specific enzymes which detach specific bonds, electrochemical means to detach the linker bonds, and/or a combination of the above techniques.

Various methods can be used to detach or cleave SERS labels from DNA fragments. There have been extensive research in the study of chemical binding/cleavage procedures related to nucleic acids. Specific cleavage can be achieved by chemical and enzymatic methods. For example, cyanine bromide (CNBr) splits polypeptide chains only on the carboxyl side of methionine residues. A SERS label containing methionine residues or related systems may therefore be bound to DNA fragments and cleaved in subsequent steps when desired. There are many other types of chemical and enzymatic cleavage in protein and nucleic acid chemistry. These systems can be adapted to the design of SERS labels. As examples of chemical cleavage, for 0-Iodosobenzoate the cleavage site is the carboxyl site of tryptophan residues; for hydroxylamine, the cleavage site is the asparagine-glycine bond; and for 2-nitro-5-thiocyanobenzoate the cleavage site is the amino side of cysteine residues. For an example of an enzymatic cleavage, the cleavage site for clostripain is the carboxyl site of arginine residue.

The DNA structure contains phosphate groups, amine groups, hydroxyl groups, etc. According to the present invention, the selection of the SERS label can be calculated to act as "blocking" or "protecting" systems for these chemical groups when bound to and cleaved from the DNA fragments. For example, an alpha-amino group of a component containing activated carboxyl groups can be blocked with a tert-butyloxycarbonyl (t-Boc) group. This t-Boc protecting group can be subsequently removed by exposing the peptide to dilute acid. Similar blocking groups containing specific SERS-active systems can be used as SERS labels.

The 2-cyanoethyl group has been used as a blocking group for the terminal phosphate group because it is very easily removed. This group (or SERS-active derivatives) can also be incorporated into a phosphorylating reagent.

Another example for developing SERS labels involves the attachment of amines to the terminal 5'-phosphate of unprotected oligonucleotides or nucleic acids, as described in the aforementioned article by Chu et al. The development of the aminoacridine SERS described with reference to FIG. 6 is based on this procedure.

The following examples show the selective removal of temporary protective groups from fully substituted phosphates. These groups can be used as SERS labels in DNA fragments according to the present invention:

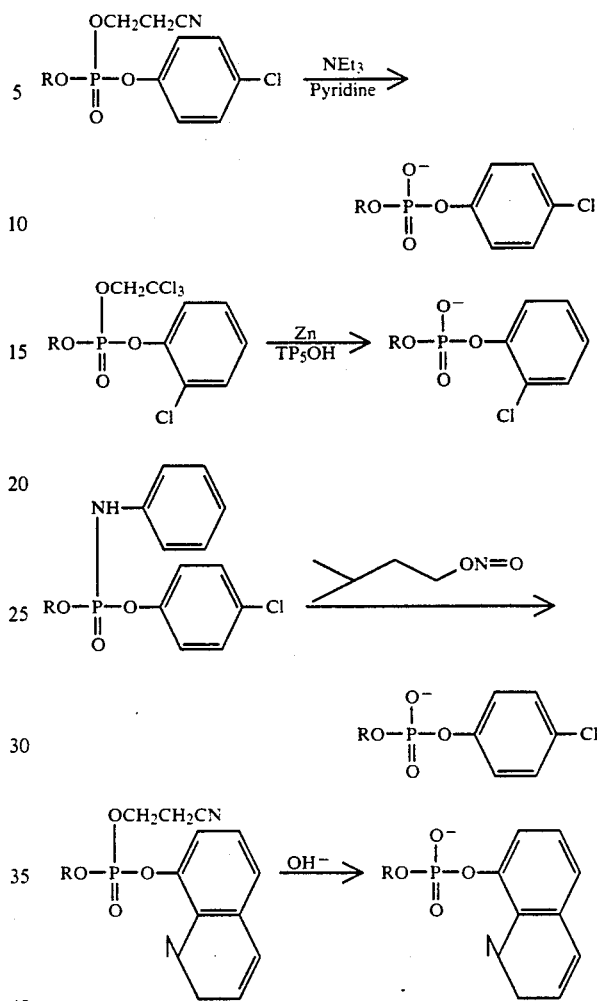

Hydroxyl groups are also present in DNA. Ethers, acetals, ketals and esters can be prepared to protect isolated hydroxyl groups. 1,2 and 1,3-diols can be protected as cyclic ethers (e.g., acetonides), cleaved by acidic hydrolysis, as cyclic esters (e.g., carbonates and boronates), cleaved by basic hydrolysis. In general, ethers, acetals, and ketals are cleaved by mild acidic hydrolysis, whereas esters are cleaved by basic hydrolysis. Some additional examples of hydroxyl blocking/protecting groups are as follows: alphanaphthyldimethylphenylmethyl ether to protect selectively the 5'-OH group in nucleosides. This compound (or a derivative having a SERS-active chemical group) can be used as a SERS label. Several substituted triphenylmethyl ethers (and derivatives) can provide selective protection for the 5'-OH group in nucleosides and used as SERS labels. An example is p-(p'-bromophenacyloxy)phenylmethyl ether. Another example is 9-(9-phenyl)xanthenyl ether (or a derivative) which protect the 5'-OH groups in nucleosides. This compound is readily cleaved by acidic hydrolysis and can be used as a SERS label.

According to the present invention, restriction enzymes, also known as endonucleases, can be selected as the SERS label in certain situations. These enzymes recognize specific base sequences in double-helical DNA and cleave both strands at specific places. In general, restriction enzymes recognize specific sequences of four to eight base pairs and hydrolyze a phoshodiester bond in the DNA strand. It thus possible to select DNA labels and probes having a SERS-active compound attached to a specific base pair sequence that can be selectively cleaved by a specific restriction enzyme.

In addition, there are other ways to cleave the SERS labels from the DNA fragments. These include attaching a SERS label or labels using a chemical bond that is specifically broken by varying certain parameters, such as pH, temperature, etc., using chemical reactions to break specific linker bonds in order to detach labels from DNA fragments, tuning a laser beam to a specific frequency to achieve specific electronic/vibrational/rotational energy to break a particular linker bond in order to selectively cleave the labels from the DNA fragment, and using the thermal energy of laser radiation to cleave the bond.

Although the invention has been described principally as a DNA sequencing apparatus and method, the same or similar procedures and methodology could be used for DNA mapping.

While advantageous embodiments have been chosen to illustrate the invention, it will be understood by those skilled in the art that various changes and modifications can be made therein without departing from the scope of the invention as defined in the appended claims.

What is claimed is:

1. An apparatus for analyzing DNA comprising:
a SERS label attached to DNA fragments;
sequencer means for separating the labeled DNA fragments;
a SERS-active media, disposed within the sequencer means, and having at least one of the DNA fragments adsorbed thereon; and
Raman spectrometer means, including a light source focused onto the SERS-active media, for producing a SERS spectrum of the SERS labeled DNA fragment, the SERS spectrum having characteristics which identify the DNA fragment.

2. An apparatus according to claim 1, wherein the sequencer means a gel electrophoresis apparatus having an enclosure, the enclosure including two parallel glass plates, and the SERS-active media is a coating disposed on an inner surface of at least one of the two glass plates.

3. An apparatus according to claim 2, wherein the SERS-active coating is silver-coated $TiO_2$.

4. An apparatus according to claim 1, wherein the sequencer means a gel electrophoresis apparatus having an enclosure containing a gel, the enclosure including two parallel glass plates, and the SERS-active media are metal microparticles disposed in the gel.

5. An apparatus according to claim 1, wherein the SERS label is a dye selected from the group consisting of aminoacridine, TRIT, NBD, fluorescein, and Texas Red dye.

6. An apparatus according to claim 1, wherein the SERS label is selected from a chemical group capable of specifically attaching to one of a sugar group, a base and a phosphate group of a DNA nucleotide.

7. An apparatus for analyzing DNA comprising:
a SERS label attached to DNA fragments;
sequencing means for separating the SERS labeled DNA fragments;
means for transferring the SERS labeled DNA fragments from the sequencer means onto a moving SERS-active substrate; and
Raman spectrometer means, having a light source focused onto the moving SERS-active substrate, for producing a SERS spectrum of the SERS labeled DNA fragment, the SERS spectrum having characteristics which identify the DNA fragment.

8. An apparatus according to claim 7, wherein the transferring means is an automated blotting apparatus.

9. A method for analyzing DNA comprising:
attaching a SERS label to DNA fragments;
separating the labeled DNA fragments with a sequencer;
adsorbing at least one of the DNA fragments onto a SERS-active media disposed within the sequencer; and
producing a SERS spectrum of the SERS labeled DNA fragment with a Raman spectrometer, the SERS spectrum having characteristics which identify the DNA fragment.

10. A method according to claim 9, wherein separating the labeled DNA fragments comprises passing the DNA fragments through a gel electrophoresis apparatus.

11. A method according to claim 9, wherein separating the labeled DNA fragments comprises passing the DNA fragments through a capillary electrophoresis apparatus.

12. A method according to claim 9, wherein separating the labeled DNA fragments comprises passing the DNA fragments through a thin-layer electrophoresis apparatus.

13. A method according to claim 9, wherein separating the labeled DNA fragments comprises passing the DNA fragments through a paper electrophoresis apparatus.

14. A method according to claim 9, wherein separating the labeled DNA fragments comprises passing the DNA fragments through a thin-layer chromatography apparatus.

15. A method according to claim 9, wherein separating the labeled DNA fragments comprises passing the DNA fragments through a paper chromatography apparatus.

* * * * *